United States Patent [19]

Black et al.

[11] 4,069,912
[45] Jan. 24, 1978

[54] SUTURE PACKAGE

[75] Inventors: Seymour Black, West Hartford; David C. MacRitchie, New Milford, both of Conn.

[73] Assignee: American Cyanamid Company, Stamford, Conn.

[21] Appl. No.: 777,791

[22] Filed: Mar. 15, 1977

[51] Int. Cl.² .............................................. A61L 17/02
[52] U.S. Cl. .................................. 206/63.3; 206/227; 206/476; 206/484
[58] Field of Search ............... 206/63.3, 227, 476–477, 206/484, 608, 610, 438, 620, 631, 632, 491–492; 229/85

[56] References Cited

U.S. PATENT DOCUMENTS

| 3,876,068 | 4/1975 | Sonnino | 206/63.3 X |
| 3,939,969 | 2/1976 | Miller et al. | 206/63.3 |

Primary Examiner—George T. Hall
Attorney, Agent, or Firm—Charles F. Costello, Jr.

[57] ABSTRACT

A surgical suture label having a needle protection flap is disclosed which permits direct dispensing of the suture. An envelope having a tearing notch and a tear angle guideline across the face of the envelope is also disclosed. When the envelope is torn from the tear notch along the guideline, the needle protection flap is exposed for direct dispensing of the suture.

6 Claims, 10 Drawing Figures

SUTURE PACKAGE

BACKGROUND OF THE INVENTION

This invention relates to a suture label which permits direct dispensing of the suture and to a tearable suture envelope that can be torn from a tear notch across the face of the envelope so as to expose the label. A suture is a strand of material suitable for suturing, with or without an attached needle or needles, used for ligating or other surgical procedures.

The packaging of many commercial products is essential to the proper end use of the product and thus forms an integral part of the overall product design. The significance of packaging is most evident in the packaging of surgical sutures. It is essential that the package protect the product and maintain sterility throughout its period of potential use. Sutures may be stored in hospitals for several years, although the usual storage time is much shorter. It is essential that the package provide rapid and positive means of identification and release the product undamaged ready for use by the surgeon. There are many sizes of sutures, and many materials of construction such as catgut or polyglycolic acid for absorbables, silk, cotton, nylon, dacron, polyethylene, polypropylene, stainless steel, insulated stainless steel and other materials for use as nonabsorbables. There are several different needle types in common use including pointed straight, pointed curved, three cornered straight, three cornered curved, curved both regular and reverse cutting, and needles with side cutting edges of various types. The variations and combinations of each of these to meet the preference of many surgeons for different operative procedures means that the suture manufacturer needs to supply different suture combinations running into the thousands. The importance of positive identification and efficient, economical packaging can thus be readily appreciated.

It is also important to provide convenience to the user and limit the risk of accidently enclosing foreign items in the patient by limiting the number of extraneous packaging materials associated with use of the product in the operating theater. A count is often kept to ensure that each item is accounted for and removed from the operating field. Considering the ramifications of enclosing such material in the patient accidently during surgical procedures, it is obviously essential to minimize this hazard.

It is also important that the surgical package properly present the needles suitably oriented within the package so that the user can rapidly and reliably grip the needle with the hand or with needle forceps in the proper position for immediate use.

It is important also, to provide a standard packaging format for all suture materials to limit confusion on the part of the user during surgical procedures. Over the years a multitude of package styles has evolved that has detracted from user convenience and operating room efficiency. For purposes of storage in the hospital as well as economy of manufacture, it is highly desirable that as many suture combinations as feasible be packaged in a minimum number of different package styles and shapes and storage units. It is quite common to package 3 dozen identical sutures in a box. It is convenient to have most of the boxes about the same size and shape, so that the hospital may store them most conveniently. It is also convenient from the manufacturers stand point to be able to reduce his inventory of box sizes and to be able to use the same components for the maximum number of suture combinations in the product line.

It is essential that a package containing a surgical needle or needles, protect the suture from contact with the sharp point or cutting edge of the needle which could partially cut the suture or the package. Also the armed needle edges and point need to be protected so as to maintain their sharpness.

These requirements are so rigorous and of such importance that many different package designs have been tried. For example, see U.S. Pat. No. 3,959,947; U.S. Pat. No. 3,939,969; U.S. Pat. No. 3,876,068; U.S. Pat. No. 3,869,044; U.S. Pat. No. 3,728,829; U.S. Pat. No. 3,444,994; U.S. Pat. No. 3,202,273; U.S. Pat. No. 2,949,181; and Canadian Pat. No. 705,232. These patents are incorporated herein by reference. Generally, these patents disclose surgical suture or sutures packaged in a plastic or foil strippable envelope. Contained in the strippable envelope is an inner envelope or pouch, which is sterile. The suture strand has been formed into various configurations of coils and loops, contained in or on various retainers, labels, or reels, within the inner envelope. The suture is normally prepared for the surgeon by stripping the outer envelope and transferring the inner envelope by sterile forceps, or by projecting it across a sterile barrier, into the sterile areas of the operating room. The inner envelope is opened at the time of use.

The inner envelope and label of the present invention have advantages over these prior art patents. After tearing the inner envelope of the present invention, the label is exposed. The label can then be used for direct dispensing without extracting it from the inner envelope. Access to the suture is provided from the label by a needle protection flap which is lifted after tearing the inner envelope.

Because the inner envelope and label remain together after opening, the proliferation of packaging materials within the immediate area of the operation or other surgical procedure is reduced. Further, besides direct access to the suture with or without needles, the suture is oriented within the label and inner envelope to allow immediate use when grasped by the needle holder or by hand. This is a desired operating room and surgical procedure technique, as it reduces the amount of time between extracting the suture from the label to its actual use as a suture. Still further, in most operations and surgical procedures, the materials used for the operation or surgical procedure are counted subsequent to the operation or surgical procedure. The label and inner envelope of the present invention provide a readily identifiable and countable package. Finally, the size of the needle and the type of suture strand can be printed on the inner envelope. This provides ready identification in a surgical procedure where more than one size and type of suture is used. The possibility of a mix-up in the sizes and types is also reduced because the suture is directly dispensed from the label contained in the inner envelope.

SUMMARY OF THE INVENTION

The direct dispensing surgical suture label of this invention is a one piece label. In the preferred embodiment, the label is divided by score lines into a back panel and five flaps.

The back panel is rectangular. Adjacent one of the long sides of the back panel is a strand cover flap. Adjacent the short sides of the back panel and attached by inner and outer score lines are side flaps. In the preferred embodiment, one side flap contains a needle retention slit. In an ulternative perferred embodiment, both side flaps contain needle retention slits. That is, at least one side flap contains a needle retention slit.

On the side of the back panel opposite the strand cover flap and attached by a score line to the back panel is a label cover flap and a needle protection flap. Both the label cover flap and the needle protection flap have rounded corners. The needle protection flap has a diagonal cut adjacent the label cover flap. A notch is thus formed between the needle protection flap and the label cover flap. The notch assists the needle protection flap to lift.

The strand cover flap is folded over the back panel. The side flaps are then folded over the strand cover flap. A surgical suture strand is then contained between the back panel and the strand cover flap. The end of the surgical suture is placed over and in the needle retention slit. Where the suture contains a large size needle, an additional needle retention slit in the other side flap is used to contain the point of the needle. The label cover flap and the needle protection flap are then folded over the side flaps. When the needle protection flap is lifted, the end of the surgical suture in the needle retention slit is directly dispensed from the label.

In another embodiment, the surgical suture label described above could have locking slits on the outside edge of the label cover flap and on the score line between the back panel and the strand cover flap. The label cover flap would thus lock against the inside edge of the strand cover flap.

In another embodiment, a suture package containing the surgical suture label described above has been discovered. The suture package consists of a sealed envelope having a tearing notch and a tear angle guideline. The tear angle guideline initiates from the tearing notch. In the preferred embodiment the tear angle guideline terminates at a score line parallel to an outer edge of the sealed envelope. The depth of the tear notch, the length of the tear angle guideline and the length and proximity of the score line to the outer edge of the envelope is not critical as long as the torn inner envelope exposes the needle protection flap of the label and the end of the surgical suture is directly dispensed from the label when the needle protection flap is lifted.

Enclosed in the sealed envelope is the direct dispensing surgical suture label described above. When the sealed envelope is opened along the tear angle guideline, the needle protection flap is exposed. When the needle protection flap is lifted, the end of the surgical suture is directly dispensed from the label.

A double envelope suture package comprising a peelable outer envelope containing the sealed envelope described above as the inner envelope and enclosed in the inner envelope a direct dispensing surgical suture level of this invention is another preferred embodiment.

DESCRIPTION OF THE INVENTION

The present suture label is, and remains, as a single piece within the inner envelope. In the preferred embodiment, the inner envelope which encloses and protects the suture in its label is notched and fits around the label so that it may be breached starting at the notch and torn open at the appropriate angle indicated, without tearing the envelope into more than one piece. The needle protection flap of the label is exposed during the tearing operation. The needle protection flap may be lifted with the hand or with the needle holder, exposing the needle in its correct orientation. The needle is grasped with the hand or needle holder and pulled gently and evenly, dispensing the suture. The present invention, and its advantages are also apparent from detailed descriptions of certain embodiments thereof which follow.

The 5 or 6 panel cover is designed to protect the strand and envelope from damage by the needle. A notch and slits are specifically located, between the label cover flap and the needle protection flap, and on the side flaps, respectively. The size and orientation of the notch and slits assist to hold the needle in proper orientation, and to aid the grasping and the dispensing of the needle with needle holders.

The lable is preferably of a sterilizable paper, of about 90 lb. weight, capable of withstanding alcoholic solutions, heat, steam, gas, or radiation sterilization without adverse effects. The paper may be coated with about ½ mil polyethylene so it is heat sealable. Such paper is known in the trade and is readily available. Sealing, if desired, may be by heat dies, or heat may be internally generated by ultrasonic means.

Figure 9:
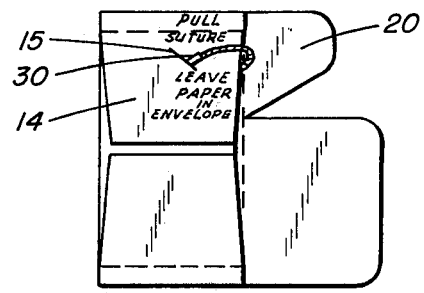
FIG. 9 shows the positioning of the suture in the side flap needle retention slit.

An important aspect of the present invention is having a tearable foil envelope that can be torn from a tear notch across the face so as to expose the label, with part of the label being lifted to permit direct dispensing of the suture — that is, the suture, usually with a needle, may be pulled out of the label while the label remains in the envelope. Note the tear notch is at such a location that the label is retained in the foil envelope by an untorn corner. This avoids clutter in the operating room, as the entire label, and package assembly, though torn, is in a single piece. FIG. 9 of U.S. Pat. No. 3,876,068 teaches a tear notch for a surgical suture package. This patent is incorporated herein by reference.

The inner envelope and suture are both protected from armed edges of the needle by the strand cover flap and the needle protection flap, respectively.

Figure 6:
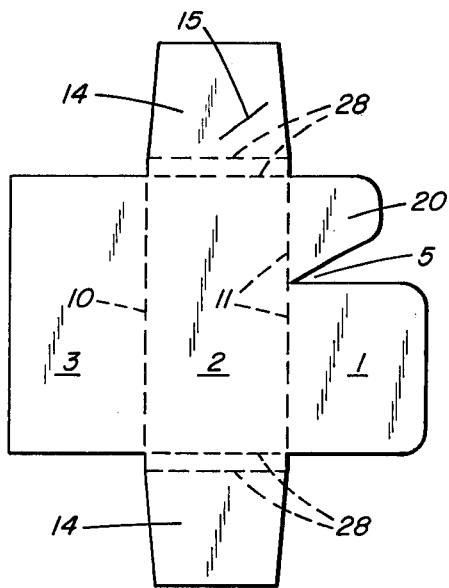
FIG. 6 is a front view of the suture label.

The label e.g., in FIG. 6, consists of six panels with the back panel accomodating loop or 8 winding of the sutures.

Figure 10:
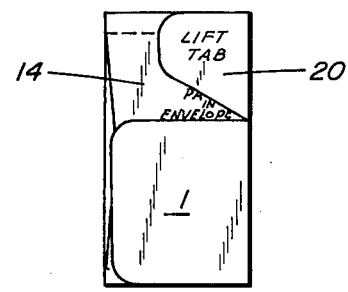
FIG. 10 describes the label cover flap and the needle protection flap folded over the side flaps of FIG. 9.

The prepared suture is shown in FIG. 10. The suture is enclosed and sealed in a notched 21 inner envelope 25 which is shown in FIG. 2. The inner envelope in turn is sealed in a strippable outer envelope 31 shown in FIG. 1.

The inner envelope may conveniently be made of a moisture proof material such as a 25 Lb., calendered, bleached, pouch paper laminated with about a ½ mil of polyethylene to a metallic foil such as about a 1 mil aluminum foil which is again laminated to 1 mil polyethylene as an inner sealable layer. Such a material is disclosed in U.S. Pat. No. 3,728,839, incorporated herein by reference. Such material is essentially moisture proof so that synthetic absorbable sutures such as those of polyglycolic acid are protected from hydrolitic degradation. The same material may be used for the packaging of catgut sutures which are packaged with a desired quantity of alcohol solution to maintain plasticity. Some sutures in which the moisture content is immaterial may also be packaged in the same material to maintain consistency of use and packaging standards.

Figure 1:
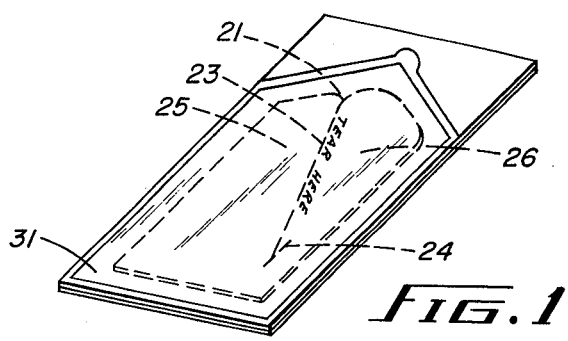
FIG. 1 shows a peelable outer envelope containing a tearable foil inner envelope.
Figure 2:
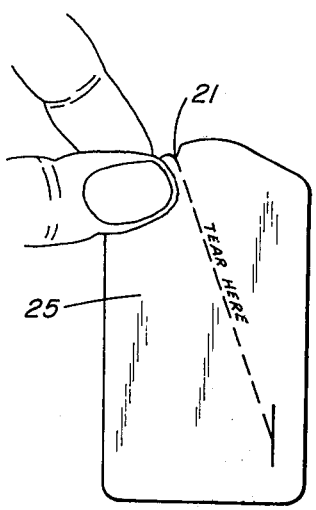
FIG. 2 shows the tearable inner envelope in position for use.

Referring to FIG. 1, the outer envelope 31 is peeled off. Using the tearing notch 21 as a start the user may then open the inner envelope 25 by tearing the laminate longitudinally along the dotted guideline 23 to stop line 24 without detaching the torn portion 26. This action exposes the needle protection flap 20 shown in FIG. 3. This action is enhanced by the size and shape of needle protection flap 20 in relation to the inner envelope. To aid the user in proper use of the package a tear arrow could be indicated on the dotted guideline 23.

Figure 3:
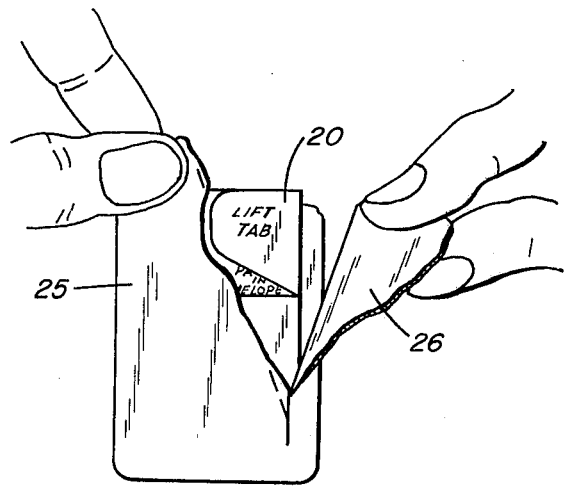
FIG. 3 shows the inner envelope being torn exposing the needle protection flap of the label.

FIG. 2 shows the inner envelope held in the position for use with the peelable outer envelope discarded. FIG. 3 shows the availability to lift of the needle protection flap 20 after the inner envelope 25 has been torn. The torn portion 26 is not detached from the inner envelope.

Figure 4:
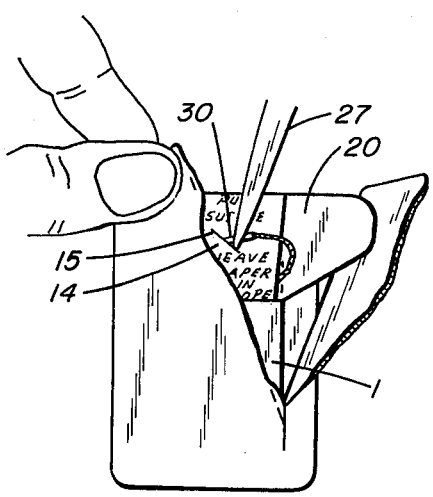
FIG. 4 shows the fully torn inner envelope and the fully opened needle protection flap exposing a needle.

FIG. 4 shows the needle protection flap 20 folded back and the needle 30 being grasped by the needle holders 27.

FIG. 4 shows part of the label cover flap 1 with the needle protection flap 20 lifted exposing the needle 30. The needle retention slit 15 in side flap 14 allows access to the needle by the needle holder 27.

Figure 5:
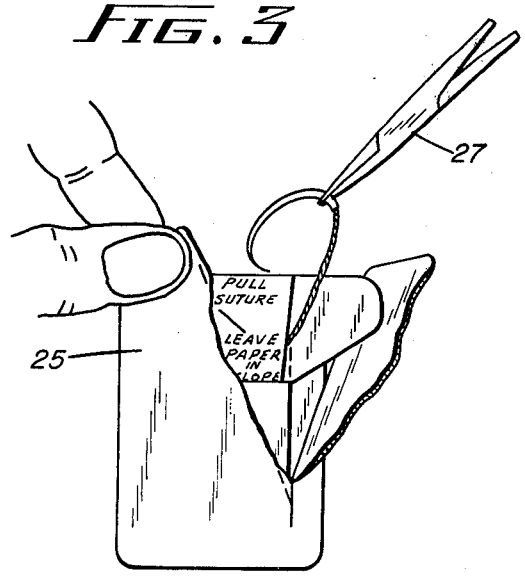
FIG. 5 describes one embodiment of the use of the direct dispensing package by removing the needle with needle holders.

FIG. 5 shows the suture being dispensed from the label package described in FIG. 4. Due to the design characteristics, the suture label is securely locked within the opened portion of the envelope 25 and the entire package remains intact. Thus no additional materials or articles other than the needle and strand are added to the operating area. Related hazards are thus minimized and accountability is simplified.

FIG. 6 shows a suture label cutout and scored from a sheet of sterilizable paper which may be coated with polyethylene for heat sealing.

As shown in FIG. 6, the suture cover consists of a back panel 2 to which is attached respectively, by score lines 10, 11, a strand cover flap 3, a label cover flap 1 and a needle protection flap 20. Side flaps 14 are attached by score lines 28 to back panel 2. Needle protection flap 20 is separated from label cover flap 1 by notch 5 and attached by scoreline 11 to back panel 2. Needle protection flap 20 is formed with rounded corners. Needle retention slit 15 anchors a needle of any size and shape in the correct orientation and position between the strand cover flap 3 and the side flap 14. The butt of the needle protrudes through the needle retention slit 15 for direct dispensing by hand or by needle holders.

Figure 7:
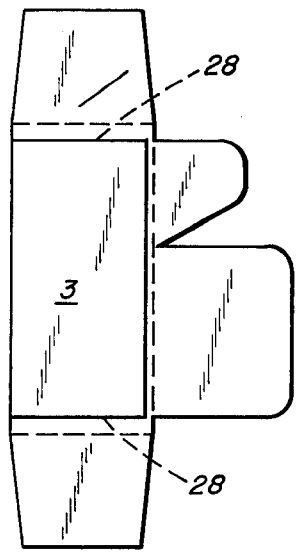
FIG. 7 shows the strand cover flap folded over the back panel of FIG. 6.

FIG. 7 shows the preferred folding of the strand cover flap 3 over the back panel 2 and between the inner score lines 28.

Figure 8:
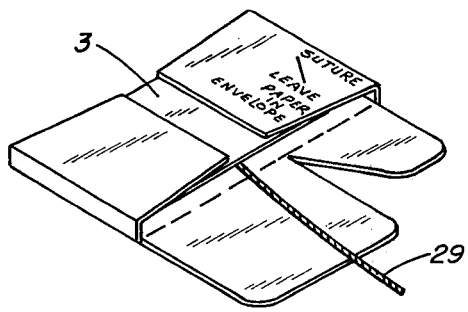
FIG. 8 shows the insertion of the suture strand into the label and the side flaps folded over the strand cover flap of FIG. 7.

FIG. 8 shows side flaps 14 folded in position over strand cover flap 3 shown in FIG. 7. The end of strand 29 is also shown in the appropriate position after inserting the strand into the label. The strand configuration can be any particular series of loops or coils that allow the strand to dispense freely without tangling. The relationship of the needled end of the strand to the rest of the coil is of no major significance.

FIG. 9 shows the proper positioning of the orientation of the butt of needle 30 in the needle retention slit 15.

FIG. 10 shows the relationship of needle protection flap 20 to the label cover flap 1 and to the side flap 14 containing the needle retention slit. Further, FIG. 10 shows the needle protection flap 20 folded over the needle thus protecting the inner envelope from damage by the butt of the needle. The needle protection flap 20 also is an aid in keeping the needle properly oriented in the label during processing or transit.

We claim:
1. A direct dispensing surgical suture label comprising
    a back panel;
    a strand cover flap adjacent said back panel;
    two side flaps adjacent opposite sides of said back panel containing inner and outer score lines and at least one side flap containing a needle retention slit;
    a label cover flap having rounded corners adjacent said back panel and opposite said strand cover flap;
    a needle protection flap adjacent said back panel and said label cover flap having rounded corners and having a diagonal cut adjacent said label cover flap forming a notch between said needle protection flap and said label cover flap;
    whereby when said strand cover flap is folded over said back panel and said side flaps are folded over said strand cover flap and a surgical suture strand is contained between said back panel and said strand cover flap with the end of said surgical suture placed over and in said needle retention slit and said label cover flap and said needle protection flap are folded over said side flaps such that when said needle protection flap is lifted, the end of said surgical suture in said needle retention slit is directly dispensed from said label.

2. A direct dispensing surgical suture label described in claim 1 having a heat sealable coating on one side.

3. A direct dispensing surgical suture label described in claim 1 manufactured from stiff sterilizable stock.

4. A direct dispensing surgical suture label described in claim 1 having locking slits on the outside edge of said cover flap, and the adjacent edge of said back panel and said strand cover flap.

5. A suture package consisting of a sealed envelope having a tearing notch and a tear angle guideline and enclosed therein a direct dispensing surgical suture label as set forth in claim 1, and in which said needle protection flap is adjacent to the tear angle guideline of said envelope, such that when said envelope is opened, said flap is exposed.

6. A double envelope suture package comprising a strippable outer envelope containing a sealed envelope described in claim 4.

* * * * *